United States Patent [19]
Szabo et al.

[11] Patent Number: 5,632,732
[45] Date of Patent: May 27, 1997

[54] NEEDLE ASSEMBLY HAVING SINGLE HANDEDLY ACTIVATED SHIELD

[75] Inventors: Sandor Szabo, Elmwood Park; Robert B. Odell, Franklin Lakes, both of N.J.

[73] Assignee: Becton, Dickinson and Company, Franklin Lakes, N.J.

[21] Appl. No.: 712,235

[22] Filed: Sep. 11, 1996

[51] Int. Cl.$^6$ .................................................. A61M 5/00
[52] U.S. Cl. ........................ 604/192; 604/187; 604/198; 604/263
[58] Field of Search ............................ 604/164, 187, 604/192, 198, 263

[56] References Cited

U.S. PATENT DOCUMENTS

| | | | |
|---|---|---|---|
| 4,909,792 | 3/1990 | Norelli | 604/192 |
| 4,966,591 | 10/1990 | Yuen | 604/192 |
| 4,982,842 | 1/1991 | Hollister | 206/365 |
| 5,055,102 | 10/1991 | Stinik | 604/192 |
| 5,116,325 | 5/1992 | Paterson | 604/192 |
| 5,207,653 | 5/1993 | Janjua et al. | 604/192 |
| 5,232,454 | 8/1993 | Hollister | 604/192 |
| 5,312,367 | 5/1994 | Nathan | 604/192 |
| 5,342,322 | 8/1994 | Nathan et al. | 604/192 |
| 5,374,255 | 12/1994 | Nathan et al. | 604/192 |
| 5,423,765 | 6/1995 | Hollister | 604/192 |
| 5,445,619 | 8/1995 | Burns | 604/192 |
| 5,490,841 | 2/1996 | Landis | 604/192 X |
| 5,584,816 | 12/1996 | Gyure et al. | 604/192 |

*Primary Examiner*—Sam Rimell
*Assistant Examiner*—Robert V. Racunas
*Attorney, Agent, or Firm*—Arthur D. Dawson

[57] ABSTRACT

A shielded needle assembly has an elongate needle with a proximal end, a distal end and a passageway therethrough. The assembly has a needle hub that has a proximal end, a distal end and an outside surface with an axial opening therethrough to receive and hold the needle with the distal end of the needle projecting distally axially. The assembly also has an elongate shield with a proximal end, a distal end and a sidewall with an elongate opening from its distal end to its proximal end. At least a section of the shield is substantially cylindrical and has an exterior surface. The shield is operable between an open position, where the needle is exposed for use by passage through the elongate opening, a closed position, where the shield substantially obstructs access to the needle, and a latched position, where the elongate opening is substantially obstructed and the shield is prevented from inadvertent movement to the open position. The assembly has a latch with an outwardly extending tab and a visual indication when the elongate opening is substantially obstructed. The assembly has a hinge including a mount for retaining the shield onto the needle hub. The shield is movable between the open position and the closed position over the needle by an off-axis pivotal movement about the hinge. The shield is latched and unlatched when in the closed position by a rotational movement of the latch with respect to the shield.

18 Claims, 14 Drawing Sheets

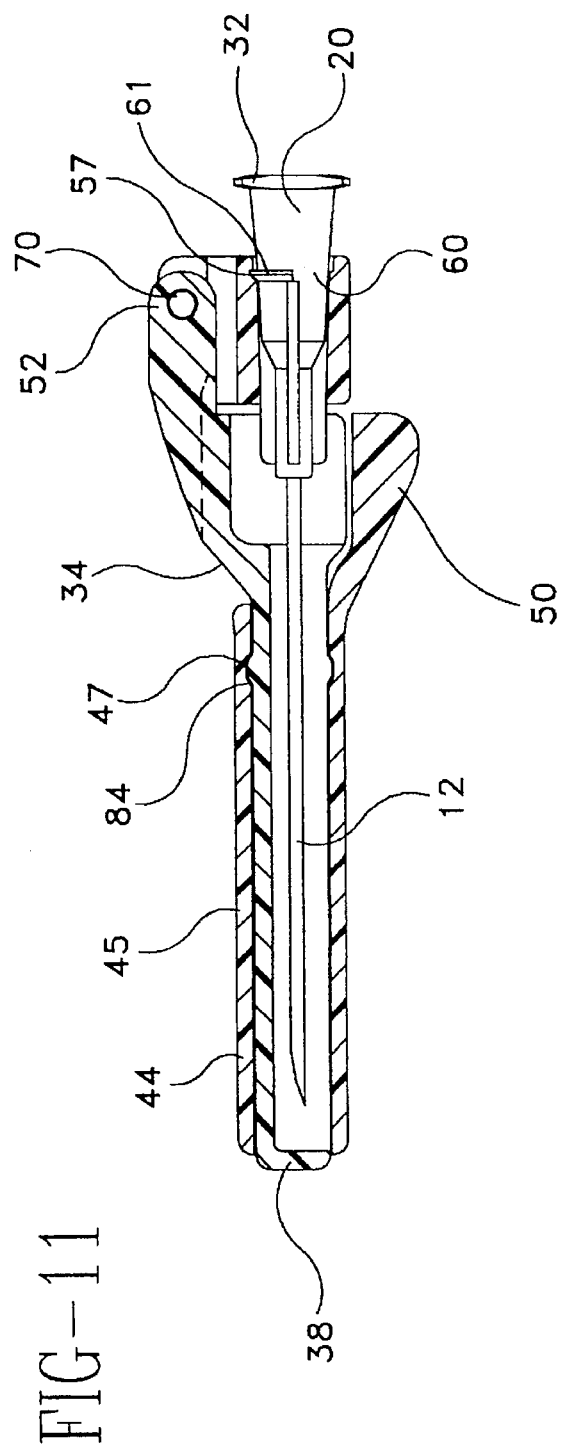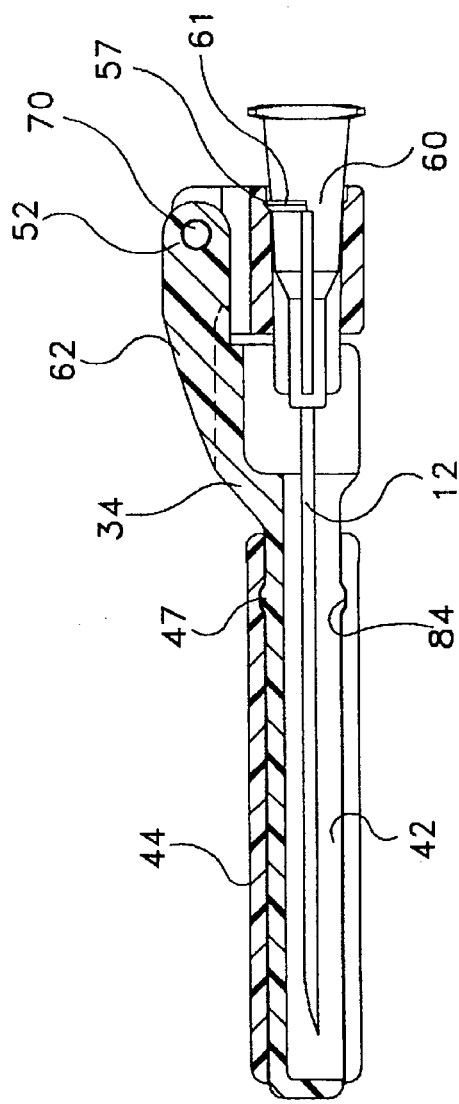

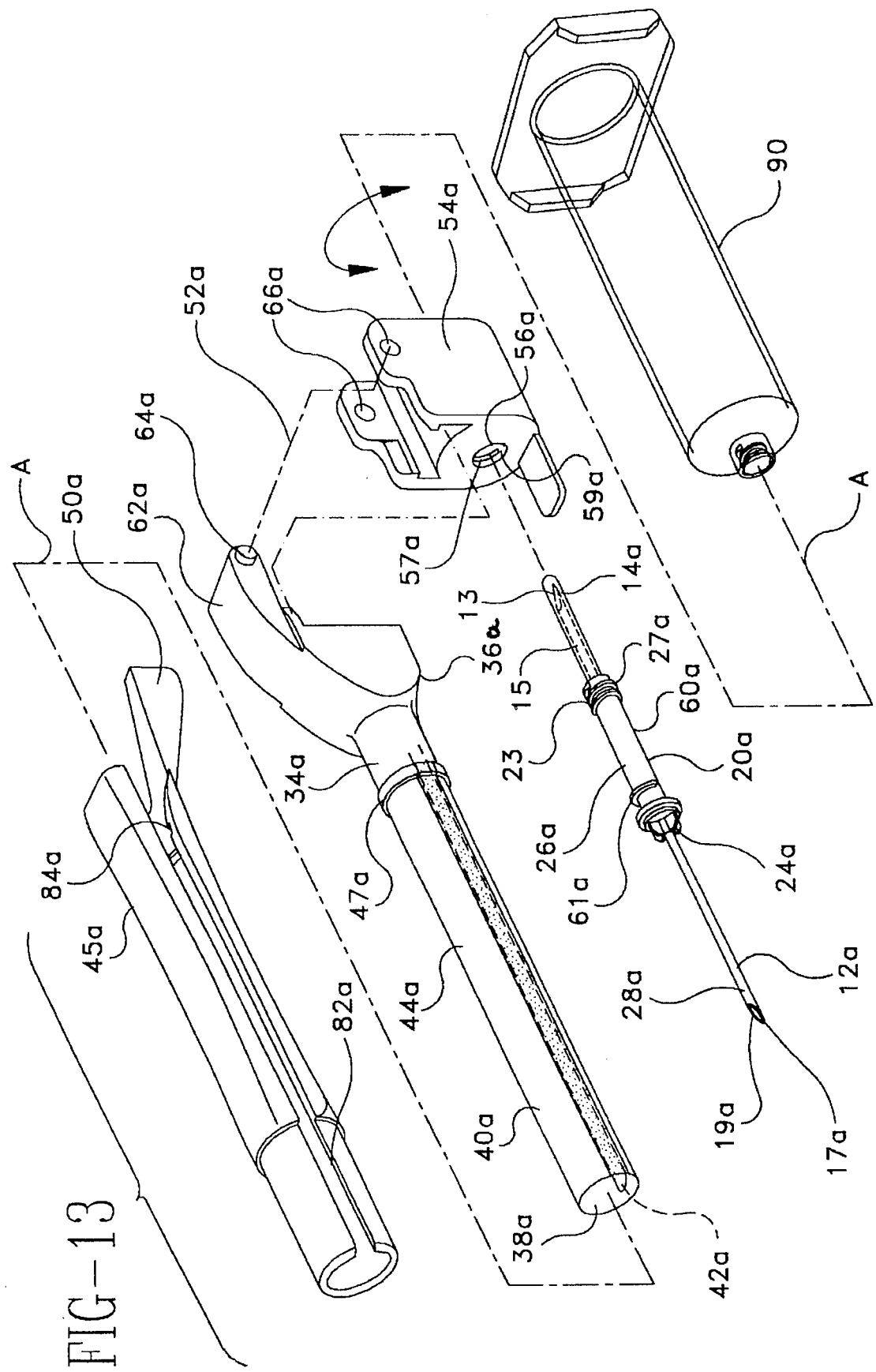

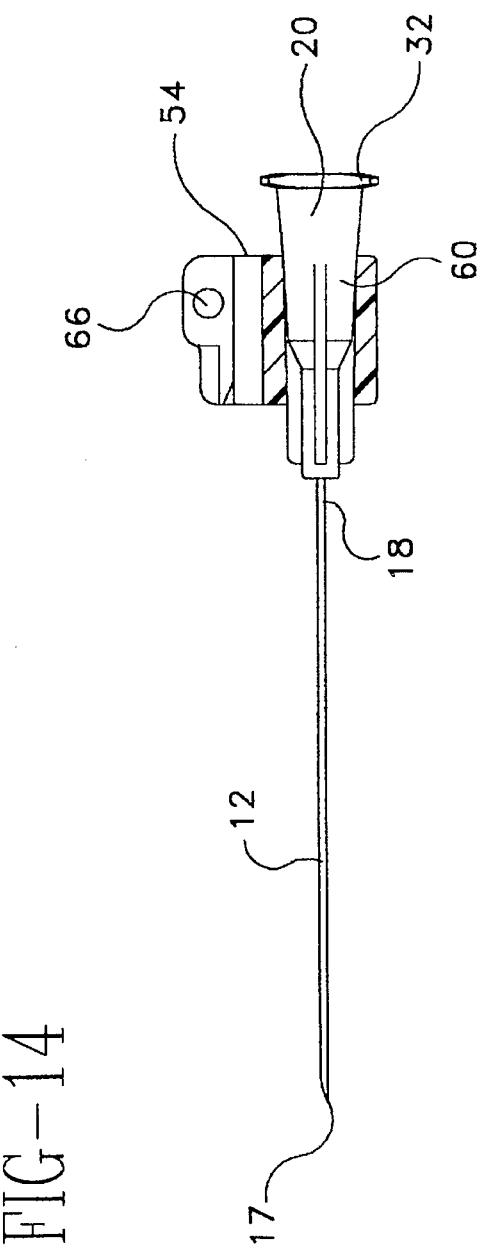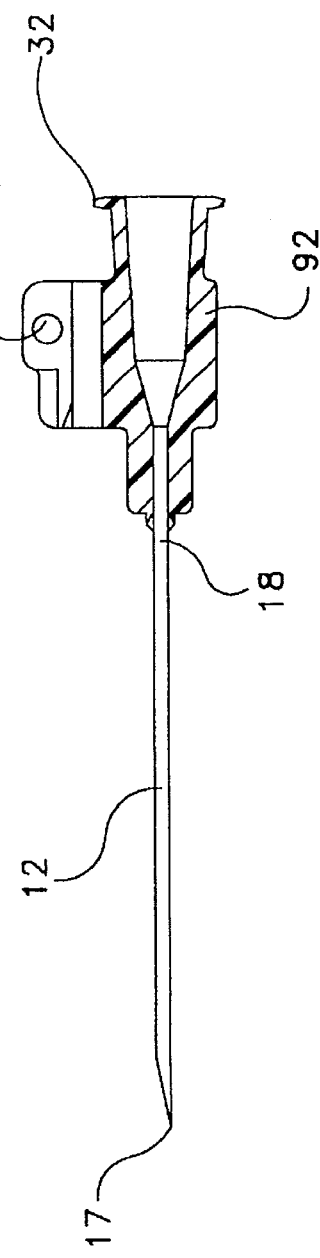

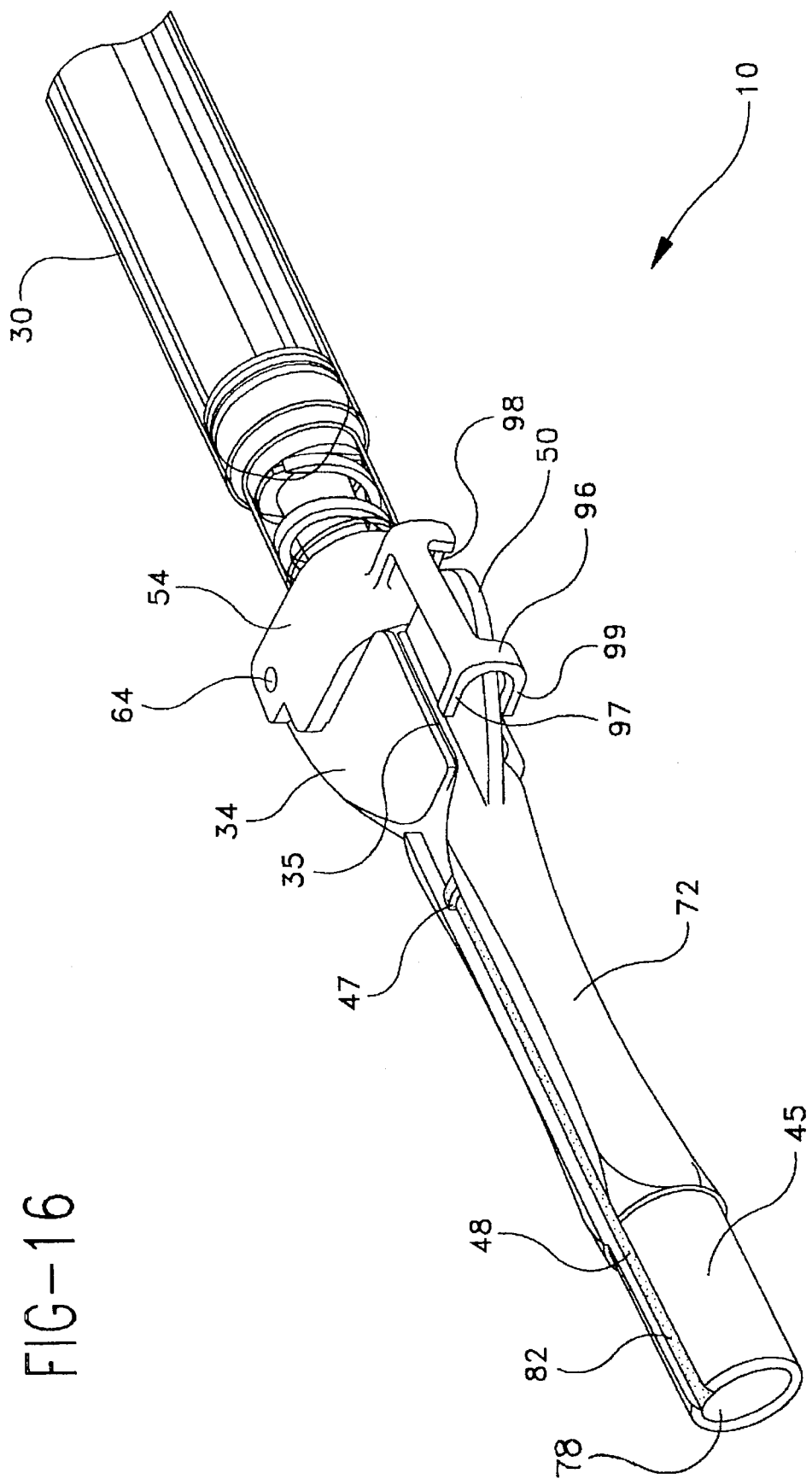

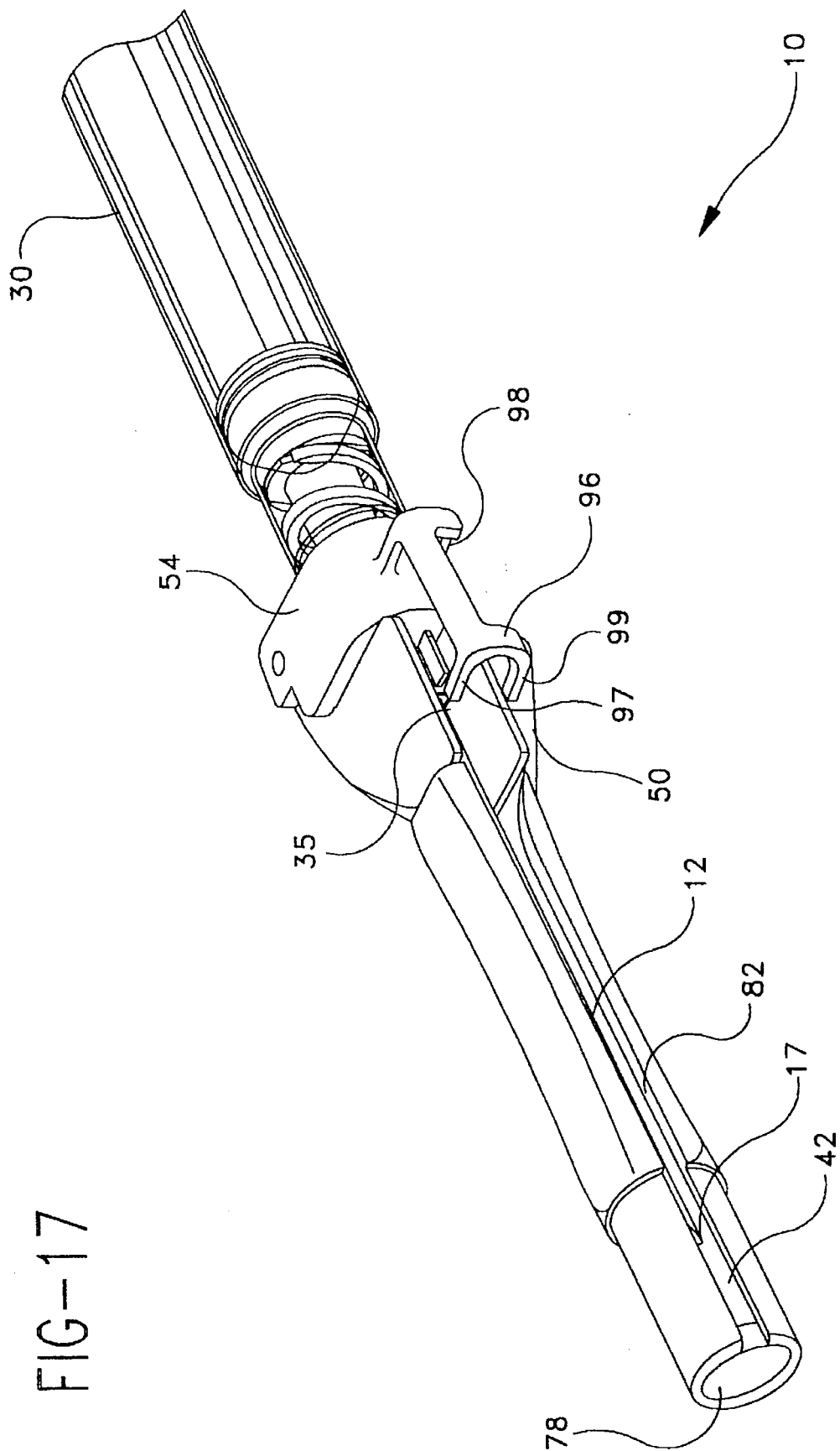

NEEDLE ASSEMBLY HAVING SINGLE HANDEDLY ACTIVATED SHIELD

FIELD OF INVENTION

The present invention relates to a protective shield for a needle and more particularly to a needle shield assembly that includes the hub of the needle, is activatable by one hand by the user and allows use of the needle on a syringe, needle holder or other fluid handling device.

DESCRIPTION OF RELATED INFORMATION

In the medical arts, sharp pointed needles are used for a variety of procedures. Devices having sharp pointed needles are used for administering fluids to patients either directly or into intravenous apparatus, and in various blood drawing applications either with syringes or with specialized holders for filling evacuated tubes.

Exposure to blood borne pathogens should be a recognized hazard by anyone associated with the medical arts. As a result of this recognition, numerous protocols for use of needles have been developed and are widely practiced. The problem of transmission of blood borne pathogens not only exists for the physician, nurse or phlebotomist using the needles, but also for support workers all through the hospital. Since most needles in use today are single-use and disposable, hospital service personnel, e.g., laundry, housekeeping, etc., are at risk from needles that are not properly handled by the users.

The needle use protocols generally dictate in detail when and how a needle is used and how it should be disposed of. The problem with many protocols for handling needles is that the protocols often require users to perform additional steps in a procedure. With the press of time and simple carelessness, certain practices regarding handling of used needles are sometimes disregarded and injuries still occur. The medical device industry has responded to the problem by producing a wide variety of sharps collectors, needle shielding devices and the like to assist practitioners in their need to reduce the occurrence of needle injuries.

Many devices have been developed for shielding needles after use to avoid exposing other workers to used needles. A representative listing of many of these devices is found in U.S. Pat. No. 4,982,842 to Hollister et al. Hollister et al. discloses a stand alone adapter that has a male and female end for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead-space" volume of the device on which the adapter is mounted, requires an additional part which increases the projection of the needle hub. Also, if bevel position is important to the intended use of the needle, the Hollister et al. invention must be carefully aligned with the needle point when the needle hub is mounted onto the Hollister et al. device.

U.S. Pat. No. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection tubes. The device disclosed by Janjua et al. mounts on the needle hub with a pivot, but since it only pivots in one plane, unless the needle point is precisely with the hub oriented during assembly, the shield may interfere in some applications.

The Hollister et al. patent and the Janjua et al. patent attempt to address the recognized need to protect medical and service personnel from needle sticks. There are several recurrent problems in varying degrees with these devices. Many of these previous devices are somewhat complex, hence are significantly more costly than an unprotected device. Many of these previous devices also increase the complexity or increase the difficulty of performing a procedure. Some others of the previous devices are so procedure specific that they preclude use of the device in certain other procedures. For these and similar reasons most of the devices disclosed in the Hollister et al. background of about ninety patents have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during manufacture. Additionally, in Janjua et al., while there is a recognition of the need to secure the cap in the closed position over the needle, all of the solutions disclose therein require additional steps such as securing the cap with an adhesive or twisting the cap. When many of these earlier shielding devices are examined, a user cannot readily tell the condition of the device by just looking at it, i.e., if the shield is latched, hence unlikely to have the needle be inadvertently exposed or simply closed, with the possibility that the needle could inadvertently be exposed.

Although there already are many shielded needle devices, there is still a need for a shielded needle device that is easily manufactured, applicable to many fluid handling devices, as well as simple and intuitive to use. Additionally, the needle shielding device should not interfere with normal practices of use. If the needle shielding device further provided a visual indication of its condition, the art encompassing these medical devices would be advanced. Such a device is described below.

SUMMARY

A preferred shielded needle assembly of the present invention includes an elongate needle with a proximal end, a distal end and a passageway therethrough. The invention has a needle hub that has a proximal end, a distal end and an outside surface with an axial opening therethrough to receive and hold the needle with the distal end of the needle projecting. The proximal end of the needle hub further includes provisions for releasably mounting the needle hub on a fluid handling device. The shielded assembly of the invention also has an elongate shield with a proximal end, a distal end and a sidewall with an elongate opening. At least a section of the shield is substantially cylindrical and has an exterior surface. The shield is operable between an open position, where the distal point of the needle is exposed for use by passage through the elongate opening; a closed position, where the shield substantially obstructs access to the needle; and a latched position, where the shield is closed and the elongate opening is substantially obstructed as well as the shield being substantially prevented from inadvertent movement to the open position. The shielded assembly has a latch that includes a visual indication when the elongate opening is substantially obstructed. The latch also includes an outwardly extending tab. The shielded assembly has a hinge including a mount for retaining the shield onto the needle hub. The mount is sized and shaped to receive at least a portion of the needle hub. The shield is movable by an off-axis pivotal movement about the hinge between the open position and the closed position, while the shield is latched and unlatched when in the closed position by a rotational movement of the latch with respect to the shield.

The shielded needle assembly of the invention offers several benefits over the existing art. A practitioner may unlatch and open the shield on the assembly of the invention with one hand without placing the hand in close proximity or beyond the sharp distal point of the needle. In a hospital pharmacy type usage, a practitioner may open the shield to fill a syringe attached to the needle assembly of the invention, then close and relatch the shield for transportation to a remote location for administration to a patient. Anyone encountering the filled and reshielded syringe with the shielded needle assembly of the invention can readily visually ascertain whether or not the shield is merely closed or latched and unlikely to inadvertently be opened to expose the needle by simply observing the opening in the latch. The ability to visually ascertain the latched or unlatched state of the assembly of the invention is important to service personnel who may encounter an improperly disposed syringe in the course of the work. When the practitioner has completed the procedure requiring the needle, reclosing and latching is readily accomplished with one hand, without the need to place the hand in close proximity to the sharp distal point. In cases where the shielded needle assembly of the invention is used in applications that are sensitive to needle bevel orientation, the shield may be rotated about the needle hub to a position where it does not interfere with the procedure. The shielded assembly of the invention is efficient to manufacture, easy to use with standard fluid handling devices and represents an advance to the art of needle assemblies.

BRIEF DESCRIPTION OF THE DRAWINGS

FIG. 11 is a cross-sectional view of the assembly from FIG. 3 along the line 11—11;

FIG. 12 is a cross-sectional view of the assembly from FIG. 4 along the line 12—12;

FIG. 13 is an exploded perspective view of an embodiment of the needle assembly of the invention for use in blood collection with a needle holder;

FIG. 14 is a partial cross-sectional view of another embodiment of the mount and needle hub portion of the assembly of the invention;

FIG. 15 is a partial cross-sectional view of yet another embodiment of the mount and needle hub portion of the assembly of the invention;

FIG. 16 is a perspective view of a further embodiment of the needle assembly of the present invention with the shield closed and latched;

FIG. 17 is a perspective view of the assembly of FIG. 16 with the shield closed and unlatched.

DETAILED DESCRIPTION

Figure 1:
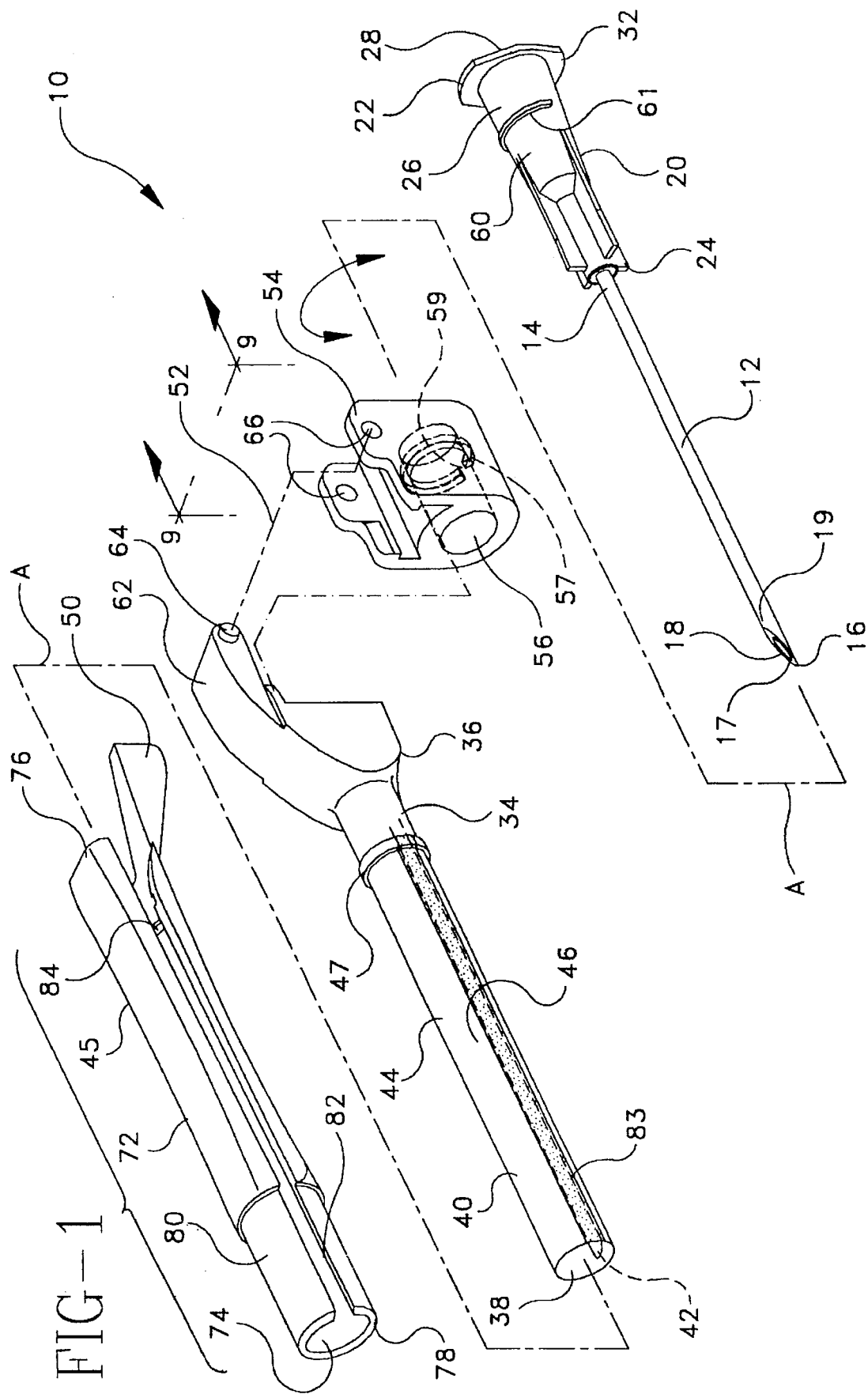
FIG. 1 is an exploded perspective view of the shielded needle assembly of the present invention.

While this invention is satisfied by embodiments in many different forms, there are shown in the drawings and herein described in detail, preferred embodiments of the invention with the understanding that the present disclosure is to be considered exemplary of the principles of the invention and is not considered to limit the invention to the embodiment illustrated. The scope of the invention is measured by the appended claims and their equivalents.

Figure 3:
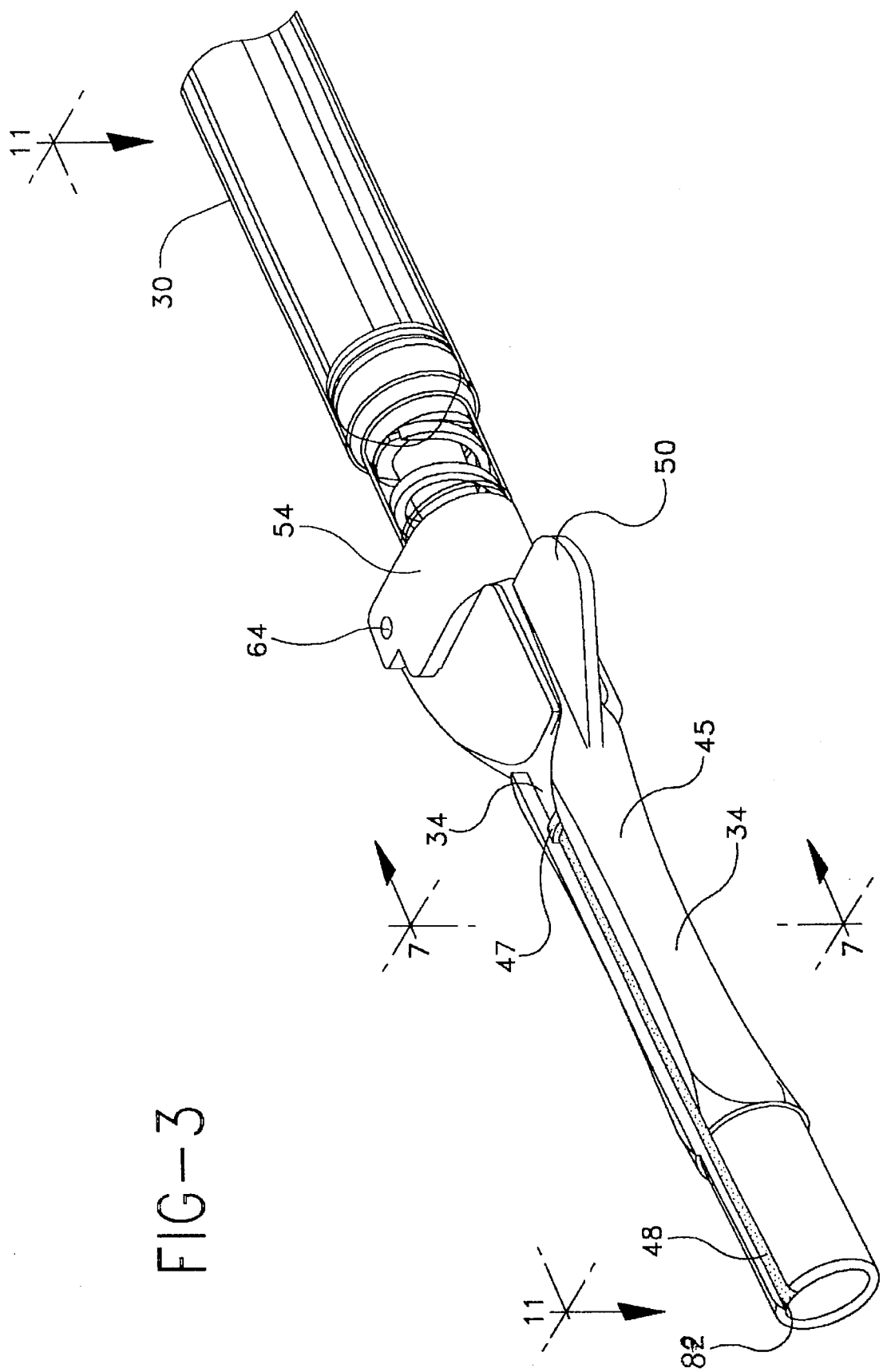
FIG. 3 is a perspective view of the assembly of FIG. 1 with the shield closed and latched mounted on a fluid handling device.
Figure 4:
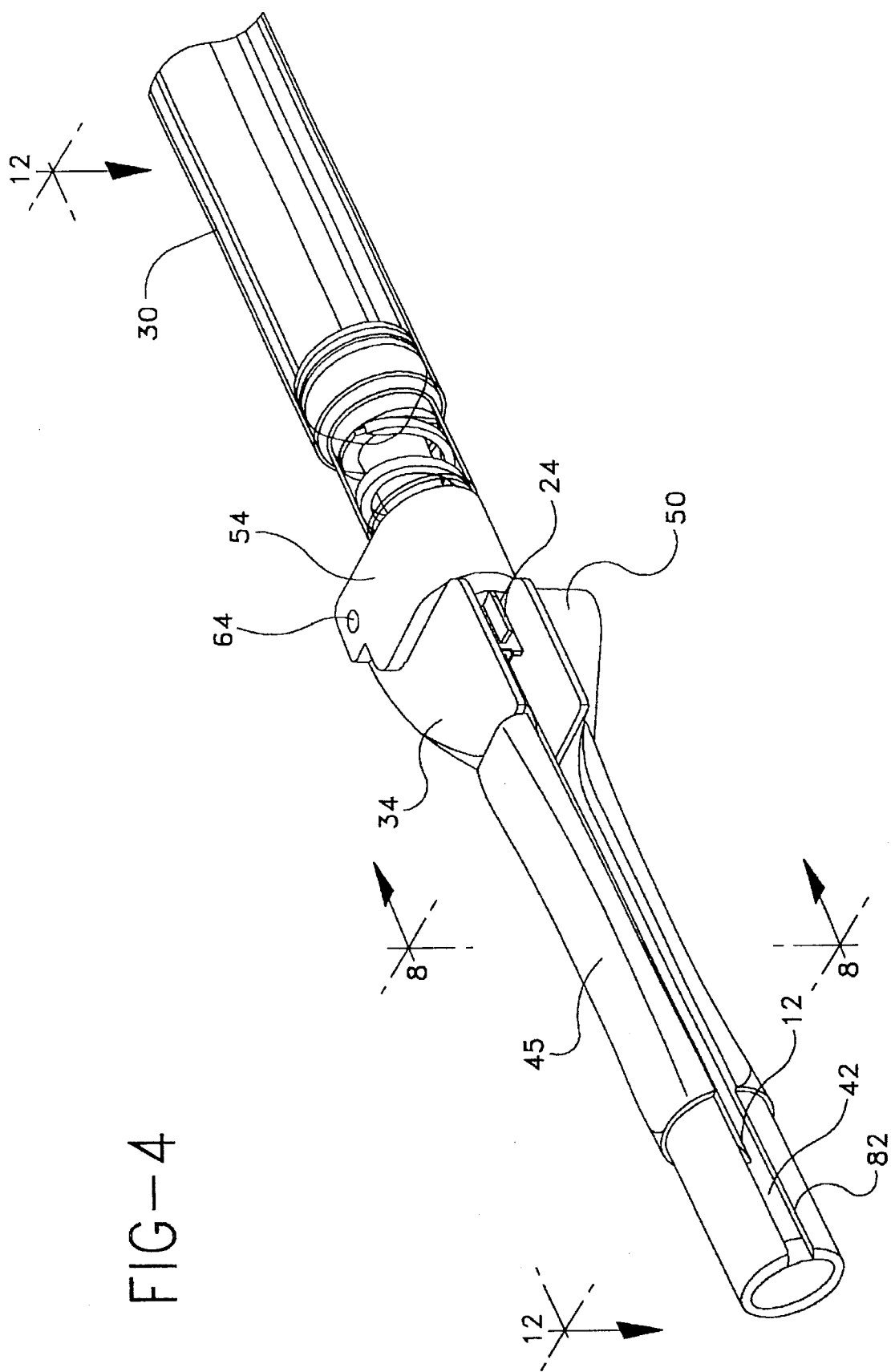
FIG. 4 is a perspective view of the assembly of the invention, analogous to FIG. 3, with the shield closed and unlatched.
Figure 5:
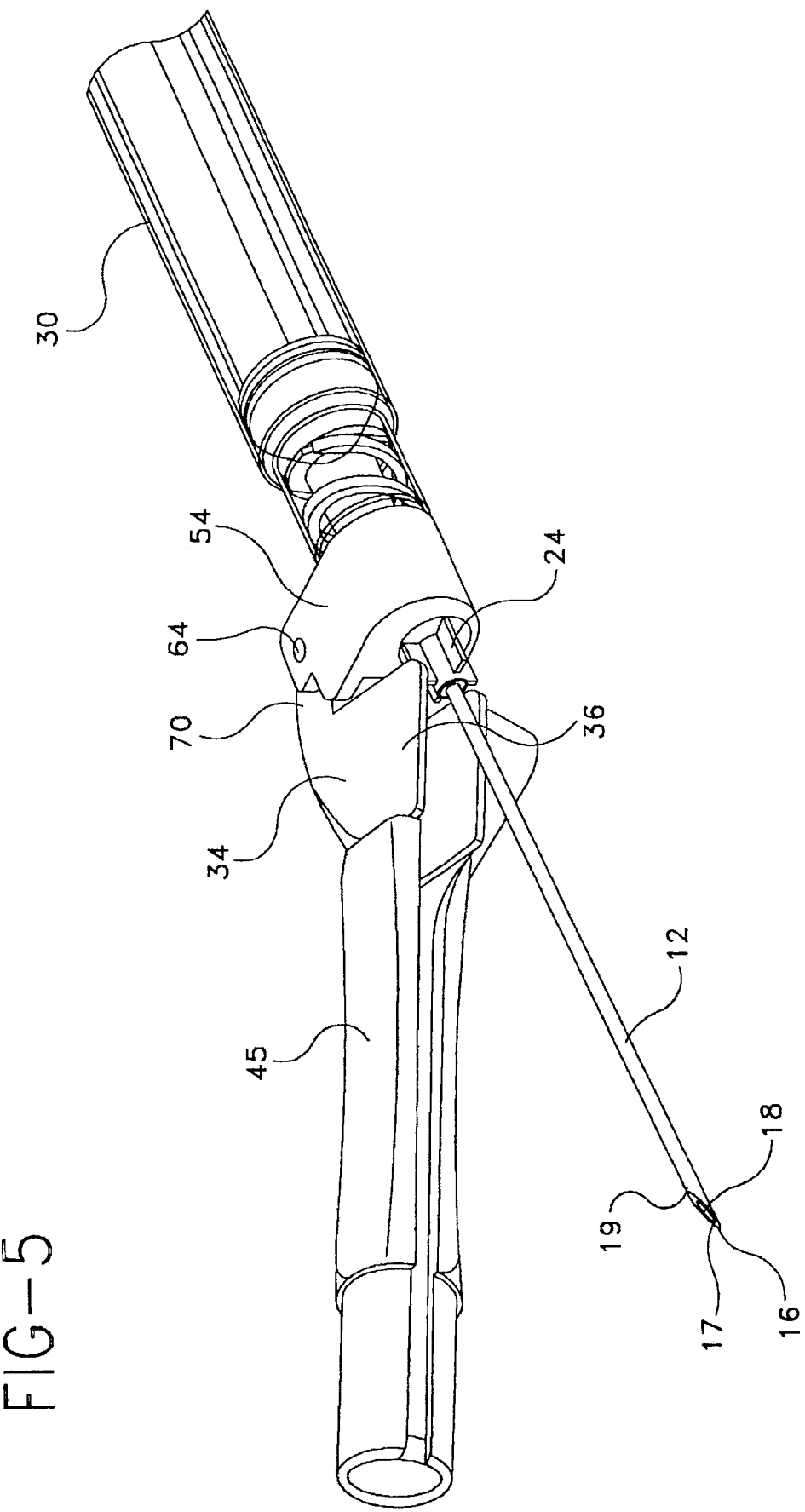
FIG. 5 is a perspective view of the assembly of the invention, analogous to FIG. 3, with the shield partially open.
Figure 6:
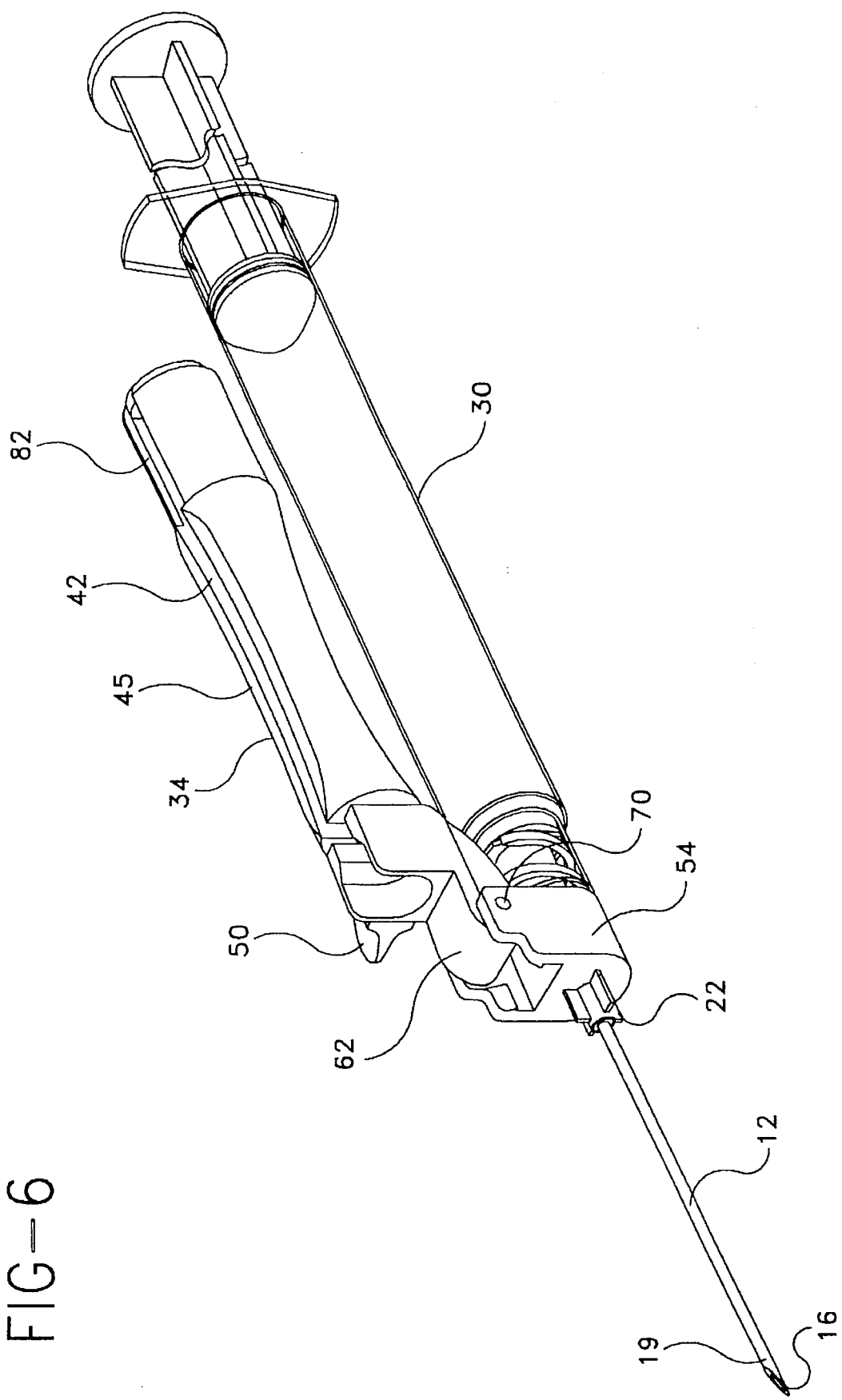
FIG. 6 is a perspective view of the assembly of the invention, analogous to FIG. 3, with the shield fully open.

Referring to FIGS. 1–12, a preferred shielded needle assembly 10 of the present invention includes an elongate needle 12 with a proximal end 14, a distal end 16, preferably a sharp point 17 with a beveled surface 19 and a passageway 18 therethrough, preferably disposed along an axis A. Assembly 10 has a needle hub 20 that has a proximal end 22, a distal end 24 and an outside surface 26. Needle hub 20 has an axial opening 28 therethrough to receive and hold needle 12 with distal end 16 projecting distally axially along axis A. Proximal end 22 of needle hub 20 includes provisions for attaching the needle hub to a fluid handling device. For the application illustrated in FIGS. 1–12, where the fluid handling device is a syringe 30, proximal end 22 preferably includes a female luer fitting 32. Assembly 10 also includes an elongate shield 34 with a proximal end 36 and a preferably closed distal end 38. Shield 34 has a sidewall 40 with an elongate opening 42, preferably extending from proximal end 36 to distal end 38. At least a section 44 of shield 34 is substantially cylindrical and has an exterior surface, 46. Exterior surface 46 of the shield has an outwardly extending shoulder 47. Shield 34 is selectively movable between an open position, as illustrated in FIGS. 5 and 6 where at least distal end 16, but preferably substantially all, of needle 12 is exposed for use by passage through elongate opening 42, and a closed position, best seen in FIG. 4 where shield 34 substantially obstructs access to needle 12. Assembly 10 also has a latched position, best seen in FIG. 3 where shield 34 is closed and, additionally, is substantially prevented from inadvertent movement to the open position with elongate opening 42 being substantially obstructed. Assembly 10 has a latch 45 that includes a visual indication 48, best seen in FIGS. 1 and 3, that elongate opening 42 is substantially obstructed. Latch 45 also includes an outwardly extending tab 50 that may be by used a practitioner to latch and unlatch shield 34. Assembly 10 has a hinge 52 that includes a mount 54 for retaining shield 34 onto needle hub 20. Mount 54 preferably has an axial passage 56 therethrough that is sized and shaped to receive at least a portion 60 of needle hub 20.

Shield 34 is movable between the closed position, illustrated in FIG. 4, and the open position, illustrated in FIGS. 5 and 6, by an off-axis pivotal movement about hinge 52. Preferably, as seen in FIGS. 1, 5 and 6, hinge 52 includes an arm 62 with two perpendicularly extending pegs 64. Mount 54 has two holes 66 sized and disposed to receive pegs 64 to form a pivot 70 and to attach shield 34 onto mount 54. Shield 34 is movable between the open and closed positions with respect to mount 54 about pivot 70. Alternatively, pivot 70 may be formed by having the pegs extending inwardly from mount 54 and disposed to engage recesses in arm 62.

Referring again to FIG. 1, latch 45 preferably includes an elongate cylinder 72 with an inside surface 74. Cylinder 72 has a proximal end 76, a, preferably open, distal end 78 and a sidewall 80 with an elongate slot 82 from proximal end 76 to distal end 78. Latch 45 is positioned on cylindrical section 44 of shield 34 so that cylinder 72 is substantially coaxial with cylindrical section 44 of the shield. Cylinder 72 has a circumferential groove 84 in inside surface 74 that is disposed and sized to engage shoulder 47 and retain latch 45 on shield 34 while allowing an annular rotation of latch 45 with respect to cylindrical section 44. Outwardly extending tab 50 is preferably located distally on latch 45 to facilitate the practitioner's rotation of latch 45 to latch and unlatch the shield.

Figure 7:
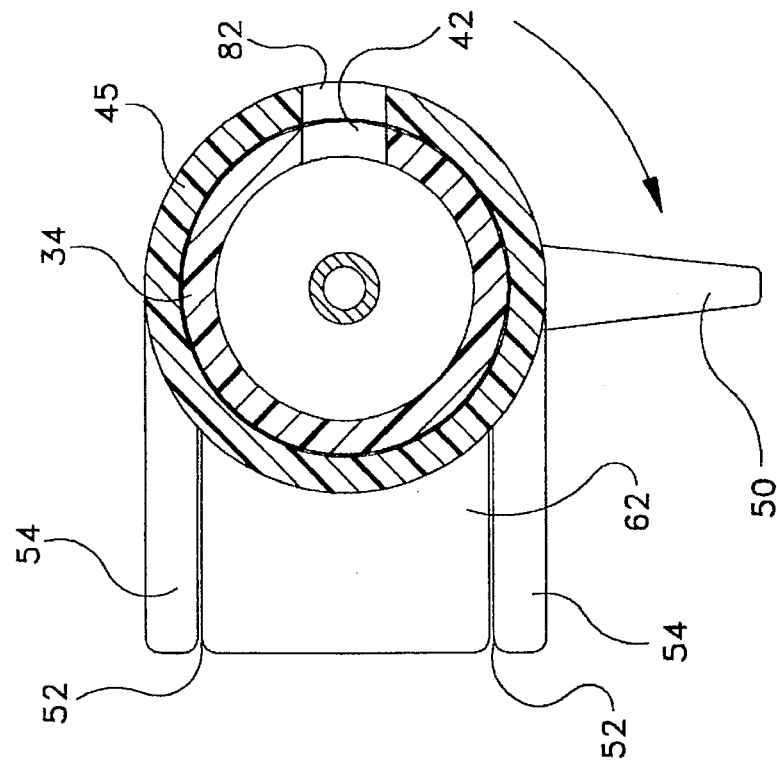
FIG. 7 is a view of the assembly of the invention taken from FIG. 3, along the line 7—7, with the shield closed and latched.
Figure 8:
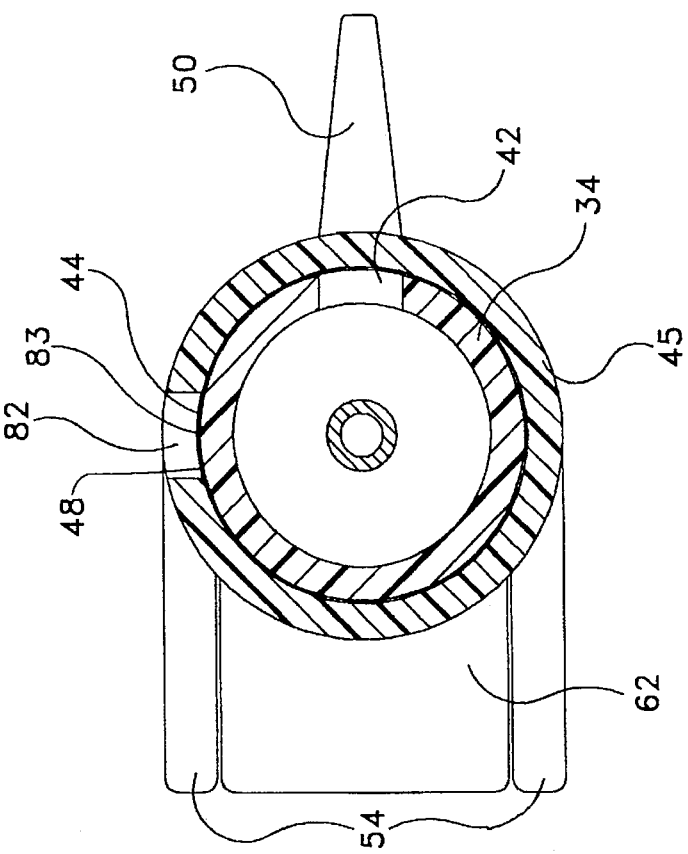
FIG. 8 is a view of the assembly of the invention taken from FIG. 4, along the line 8—8, with the shield closed and unlatched.

FIGS. 1, 3 and 4 illustrate visual indication 48 that elongate opening 42 is substantially obstructed when shield 34 is latched. The annular rotation of latch 45 with respect to shield 34 is illustrated in FIGS. 7 and 8. In FIG. 7, elongate slot 82 of the latch is not aligned with elongate opening 42 in the shield and the substantially preventing shield 34 from being pivoted about the hinge to expose needle 12. Visual indication 48 is provided by observation of a portion of cylindrical section 44 in elongate slot 82 when latch 45 is rotated with respect to shield 34 so that elongate slot 82 in the latch is not aligned with elongate opening 42 in the shield. In FIG. 8, latch 45 is shown rotated clockwise with respect to shield 34 and elongate slot 82 is substantially aligned with elongate opening 42. When latch 45 is in the position illustrated in FIG. 8, shield 34 may be pivoted about hinge 52 so that needle 12 is exposed for use. Preferably, at least a portion 83 of cylindrical section 44 of the shield has a color that contrasts to a color of latch 45 so that an observer easily visually can determine if the shield is latched or merely closed. Alternatively, latch 45 can have a contrasting color to the entire shield 34 to provide the visual indication that elongate opening 42 is obstructed by the latch. FIG. 11 illustrates the positioning of latch 45 on shield 34 and the position of outwardly extending tab 50 when elongate opening 42 is obstructed, i.e., shield 34 is latched. FIG. 12 illustrates the positioning of latch 45 on shield 34 after rotation of latch 45 with respect to shield 34 so that elongate opening 42 is not obstructed, i.e., shield 34 is closed, but is free to pivot about hinge 52 to expose needle 12.

Figure 10:
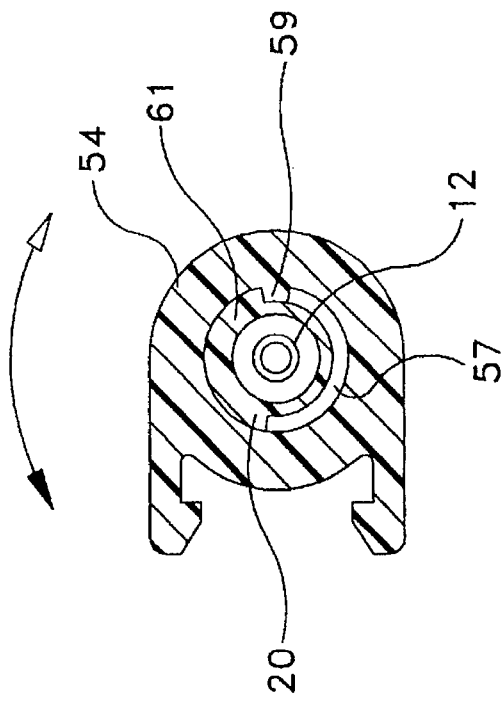
FIG. 10 is a cross-sectional view of the mount and needle hub portion of the assembly, analogous to FIG. 9, with the mount rotated 90° with respect to the needle hub.
Figure 9:
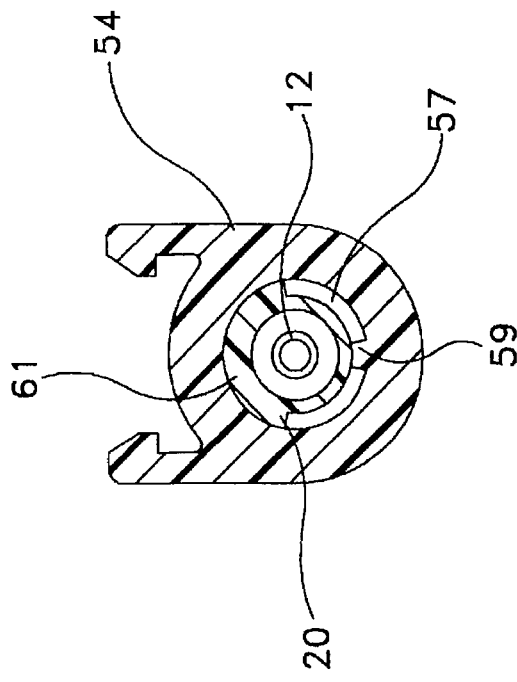
FIG. 9 is a cross-sectional view of the hub portion of the assembly from FIG. 1 along the line 9—9.

As shown in FIGS. 1, 9 and 10, mount 54 has, preferably axial, passage 56 to receive at least portion 60 of needle hub 20. Passage 56 preferably includes a circumferential groove 57 that is sized and disposed to engage a preferred external projection 61 located on portion 60 of needle hub 20 to retain mount 54 on needle hub 20 and preferably allow annular rotation of mount 54 about needle hub 20. Preferably, groove 57 includes a stop 59 to limit the annular rotation of mount 54 about needle hub 20 to less than about one rotation, to facilitate threading and unthreading hub 20 to fluid handling devices. FIGS. 9 and 10 illustrate the rotation of preferred mount 54 with respect to needle hub 20 and indicate stop 59 to limit the movement to less than about one rotation. The preferred ability to rotate mount 54 with respect to needle hub 20 allows a practitioner to rotate the shield to a position where it does not interfere with the procedure to be practiced. This ability to move the shield with respect to the needle hub is important to procedures that are sensitive to needle bevel position such as intravascular penetrations for blood drawing and the like.

FIG. 13 illustrates an alternative preferred embodiment of the assembly for use with a needle holder useful for drawing blood samples with evacuated tubes. In this embodiment there are elements similar in structure and function to the catheter and needle assembly of FIGS. 1–12. Accordingly, substantially similar components that perform substantially similar functions are numbered identically to those of FIGS. 1–12 except that the suffix "a" is used to identify those components in FIG. 1–12.

Referring to FIG. 13, preferred shielded needle assembly 10a of the present invention includes an elongate needle 12a with a proximal end 14a and a distal end 16a. In this embodiment, needle 12a with passageway 18a therethrough has a sharp distal point 17a with a beveled surface 19a and a sharp proximal point 13 that has a resilient valve 15 thereover, preferably disposed along axis A. Assembly 10a has a needle hub 20a that has a proximal end 22a, a distal end 24a and an outside surface 26a. Needle hub 20a preferably has an axial opening 28a therethrough to receive and hold needle 12a with distal end 16a projecting distally axially and proximal end 14a projecting proximally along axis A. In this embodiment, needle hub 20a includes external threads 23 on outside surface 26a for attaching the needle hub to a needle holder 90 illustrated in FIG. 13.

In the alternate preferred embodiment of FIG. 13, analogous to the embodiment shown in FIGS. 1, 9 and 10, mount 54a has passage 56a, that is preferably axial, to receive at least portion 60a of needle hub 20a. Passage 56a preferably includes a circumferential groove 57a that is sized and disposed to engage an external projection 61a located on portion 60a of needle hub 20a to retain mount 54a on needle hub 20a and allow annular rotation of mount 54a about needle hub 20a. Preferably, groove 57a includes a stop 59a to limit the annular rotation of mount 54a about needle hub 20a to less than about one rotation, to facilitate threading and unthreading hub 20a to needle holder 90.

The ability to rotate mount 54a with respect to needle hub 20a allows a practitioner to rotate the shield to a position where it does not interfere with the procedure. This rotatability is particularly important in phlebotomy procedures. In performing a phlebotomy, the practitioner generally aligns the needle longitudinally with the target blood vessel at a shallow angle to the patient's skin. Most practitioners also align needle bevel surface 19a upwardly, i.e., away from the patient's skin. If the needle shield was not able to be rotated with respect to the needle hub, the needle bevel would need to be oriented during the manufacturing process, otherwise, the location of open shield would interfere with the procedure. In the present invention, the rotation of the shield with respect to the needle hub allows the normal needle/needle hub assembly process to be used without imposition of a bevel orientation requirement thus maintaining the efficiency of the normal needle/needle hub assembly process.

FIGS. 14 and 15 illustrate embodiments of the invention related to the invention of FIGS. 1–12. FIG. 14 illustrates an embodiment of mount 54 and needle hub 20 from assembly 10 for applications where needle point bevel orientation is not significant. All of the various components of the embodiment of FIGS. 1–12 present in this embodiment are identical, hence the reference characters used are identical to those in FIGS. 1–12. In this embodiment, needle hub 20 is fixedly attached to mount 54 in passage 56. Suitable methods of fixedly attaching the mount to the needle hub include, but are not limited to, adhesive bonding, mechanical interference fit, a thermal weld, a solvent bond, a mechanical snap-fit and the like.

In FIG. 15, the structures of the needle hub and the mount are integrally formed as a single structure 92, all of the other various components present in this embodiment are identical to those of the embodiment of FIGS. 1–12 are identical, hence the reference characters are identical to FIGS. 1–12.

Figure 18:
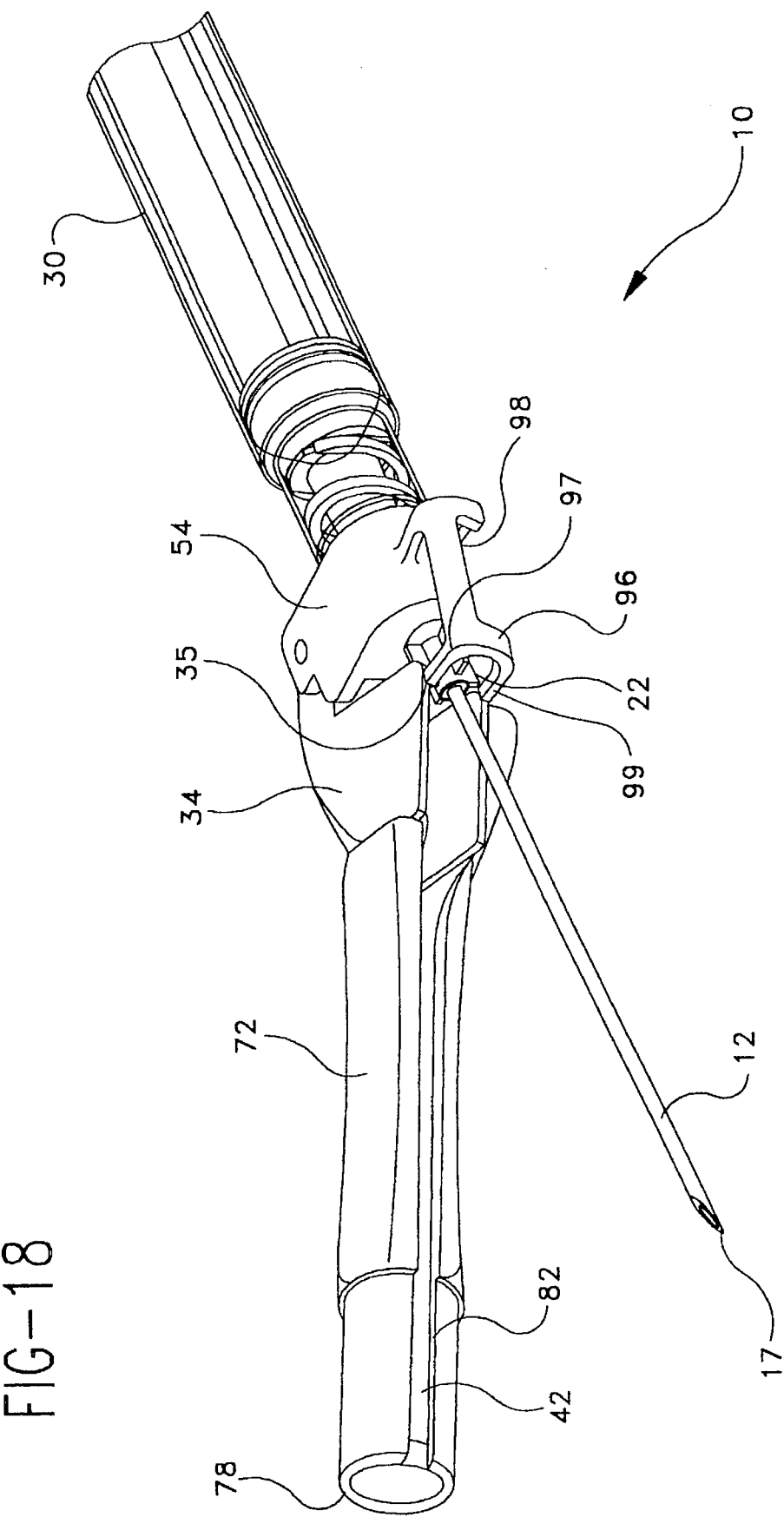
FIG. 18 is a perspective view of the assembly of FIG. 16 with the shield partially opened.

FIGS. 16–18 illustrate yet another embodiment of the assembly of the invention. In this embodiment, assembly 10 further includes a pusher 96 located on mount 54 opposite hinge 52. Pusher 96 extends distally on mount 54 and is disposed to engage a proximal portion 35 of shield 34 with legs 97 and 99. As shown in FIG. 16, pusher 96 preferably includes a recess 98 to accommodate at least part of tab 50 when latch 45 is in the latched position with elongate opening 42 being obstructed. Additionally, leg 99 also serves as a restraint to rotation of tab 50, substantially preventing inadvertent movement of latch 45 from the latched to the unlatched position. When the practitioner desires to rotate latch 45 between the latched and the unlatched position, a positive action to move tab 50 against pusher 96 deflects the pusher away from the axis to allow movement of tab 50 past leg 99 and rotate latch 45 with respect to shield 34. Referring to FIGS. 17 and 18, when tab 50 is used by the practitioner to rotate latch 45 with respect to shield 34 and unlatch the shield, pusher 96 may then be deflected toward the axis to urge shield 34 to the open position and needle 12 with the same hand.

Figure 2:
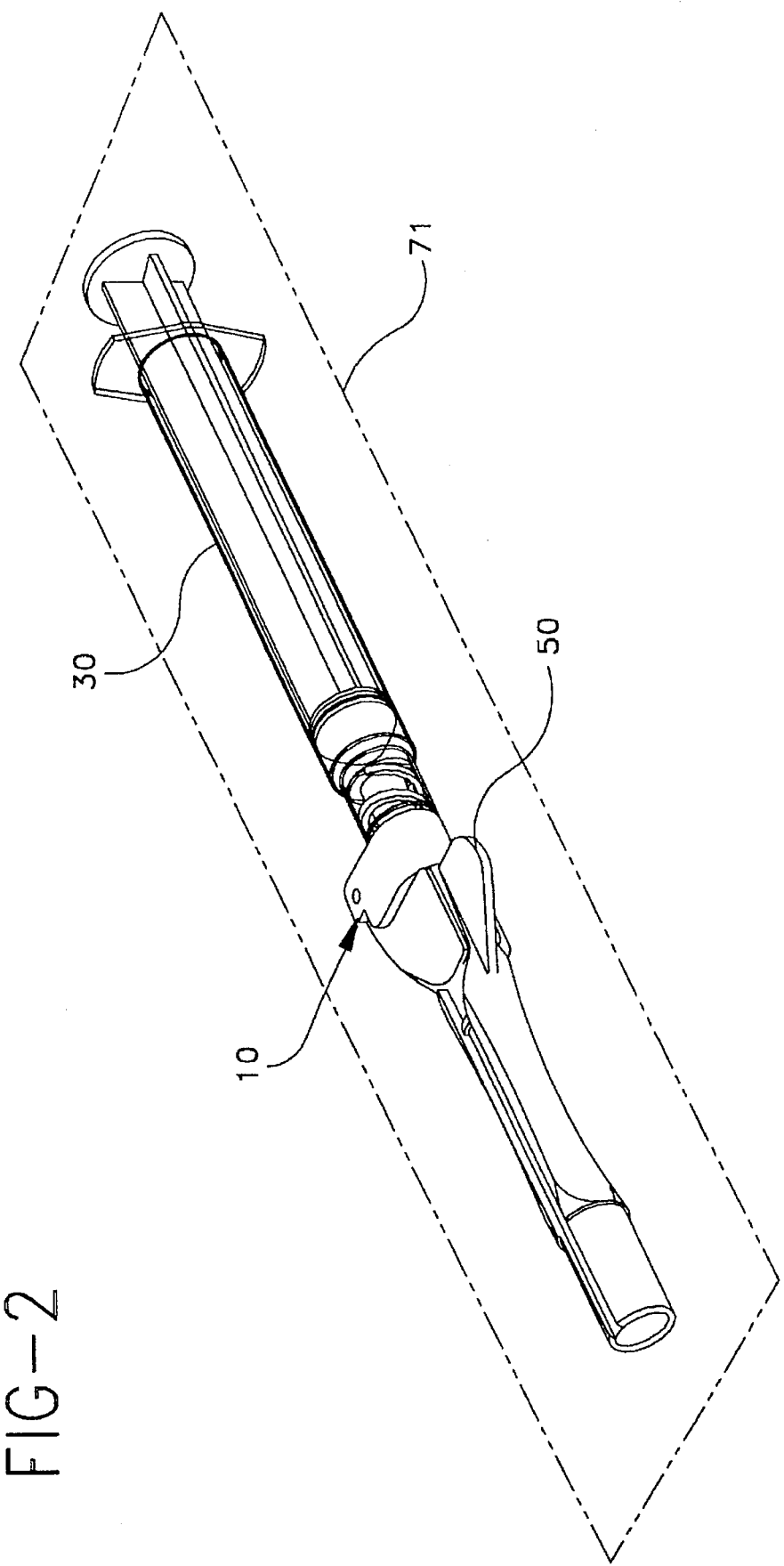
FIG. 2 is a perspective view of the assembly of FIG. 1 mounted on a syringe and placed in a package.

FIG. 2 illustrates assembly 10 with the shield in the latched position, mounted on syringe 30 and placed in a sealed package 71, as indicated in phantom, that is formed from materials substantially resistant to the passage of microorganisms. The sealed package is then preferably exposed to conditions sufficient to render any microorganisms within the package substantially non-viable. Suitable package materials include, but are not limited to, paper, plastic film, non-woven materials, combinations thereof and the like. Suitable conditions for rendering microorganisms non-viable include, but are not limited to, chemical sterilants such as ethylene oxide, hydrogen peroxide vapor and the like; and exposure to ionizing radiation such as gamma radiation, beta particles and the like. The packaged assembly is then considered to be sterile until the package is opened. When materials are selected for forming assembly 10 and package 71, there should be consideration of the particular materials compatibility with the planned sterilization conditions.

Suitable materials for forming the shield, needle hub and mount of the invention include, but are not limited to, thermoplastic polymeric resins such as polypropylene, polystyrene, polycarbonate, acrylonitrile/butadiene/styrene, and the like. Suitable materials for forming the needle of the assembly include stainless steels.

The needle assembly of the invention allows a practitioner to open and close the shield over the needle without placing his hands in close proximity to the distal point of the needle. The shielded needle assembly of the invention is particularly useful in clinical practice applications that require filling a syringe with a medication at a location remote from the location where the medication is administered to the patient. The syringe may be filled and the shield reclosed substantially without risk of damage to the needle that might be caused by a mis-replacement of a standard needle shield. Additionally, in the preferred embodiment, the shielded assembly of the invention allows annular rotation of the shield with respect to the needle in addition to the pivotal opening and closure of the shield about the hub of the needle. The rotation of the shield about the hub enables a practitioner to position the shield to substantially eliminate interference of the shield with a procedure. The visual indication of the latched state of the shielded needle assembly allows a worker who encounters the shielded assembly to visually ascertain that the shield is latched and unlike to inadvertently expose the needle. The presence of the tab and the pusher on the shielded assembly allow for one-handed operation without the need for the practitioner to place his hands in close proximity to the sharp distal point of the needle.

What is claimed is:

1. A shielded needle assembly comprising:

an elongate needle having a proximal end, a distal end and a passageway therethrough defining a axis;

a needle hub having a proximal end, a distal end and an outside surface, said needle hub having an axial opening therethrough to receive and hold said needle with said distal end of said needle projecting therefrom, said proximal end of said needle hub further including means for releasably mounting said needle hub on a fluid handling device;

an elongate shield having a proximal end, a distal end, a sidewall having an elongate opening from about said distal end to said proximal end, wherein at least a section of said shield is substantially cylindrical with an exterior surface, said shield being movable between an open position, wherein at least said distal point of said needle is exposed for use by passage through said elongate opening, a closed position, wherein said shield substantially obstructs access to said needle, and a latched position, wherein said shield is closed, said elongate opening is substantially obstructed and said shield is substantially prevented from inadvertent movement to said open position;

latch means for substantially preventing inadvertent movement of said shield including a visual indication of said elongate opening being substantially obstructed, said latch means further including an outwardly extending tab, said shield being latched and unlatched in said closed position by a rotational movement of said latch means with respect to said shield; and hinge means including a mount for retaining said shield onto said needle hub, said mount being sized and shaped to receive at least a portion of said needle hub, said shield movable between said open position and said closed position over said needle by an off-axis pivotal movement about said hinge means.

2. The needle assembly of claim 1 wherein said latch means comprises an elongate hollow cylinder with an inside surface, said cylinder having a open proximal end, an open distal end and a sidewall with an elongate slot from said proximal end to said distal end, therethrough, said cylinder further including a circumferential groove in said inside surface, said cylinder being disposed coaxially about said cylindrical section of said shield.

3. The needle assembly of claim 2, wherein said cylindrical section of said shield includes an outwardly extending circumferential shoulder on said exterior surface, said shoulder being located and sized so that when said latch means is disposed on said shield, said shoulder engages said circumferential groove thereby retaining said latch means on said shield and allowing rotation of said latch means with respect said cylindrical section, and wherein said outwardly extending tab is located distally on said latch means to facilitate said rotation.

4. The needle assembly of claim 3 wherein said at least a portion of said cylindrical section of said shield has a contrasting color to a color of said latch means so that when said shield is latched with said elongate opening being substantially obstructed, said contrasting color is visible through said elongate slot in said latch means thereby providing a visual indication that said shield is substantially prevented from inadvertent movement to expose said needle, said shield being unlatched by a rotational movement of said latch means with respect to said shield so that said elongate slot is substantially aligned with said elongate opening in said shield, thereby allowing the pivotable movement about said hinge means to expose said needle.

5. The needle assembly of claim 1 wherein said hinge means comprises at least one arm projecting proximally from said open end of said shield opposite said open slot, said arm having two perpendicularly extending pegs, and said mount having two holes therein sized and disposed to receive said pegs thereby to form a pivot and to attach said shield to said mount, said shield being movable with respect to said mount about said pivot.

6. The needle assembly of claim 1 wherein said means for releasably mounting said hub on the fluid handling device comprises a female luer fitting on said hub.

7. The needle assembly of claim 1 wherein said means for releasably mounting said hub on the fluid handling device comprises external male threads on said hub.

8. The needle assembly of claim 1 wherein said means for retaining said mount to said needle hub fixedly attach said mount to said needle hub, said means being selected from the group consisting of an adhesive bond between said needle hub and said passage, a mechanical interference fit between said needle hub and said passage, a solvent bond between said needle hub and said passage, a thermal weld between said needle hub and said passage, and a mechanical snap-fit between said needle hub and said passage.

9. The needle assembly of claim 1 wherein said means for retaining said mount to said needle hub comprises an annular groove on an inside surface of said axial passage in said mount and an external projection on said portion of said needle hub disposed and sized to engage said groove when said portion of said needle hub is positioned in said passage, said engagement of said projection and said groove thereby retaining said mount on said hub and allowing rotation of said mount about said hub.

10. The needle assembly of claim 9 wherein said groove and said projection further include limit means to limit said rotation of said mount about said hub to less than about one rotation, thereby facilitating a threading and an unthreading of said hub for mounting and dismounting of said assembly to fluid handling devices.

11. The needle assembly of claim 10 wherein said limit means for limiting said rotation of said mount about said hub includes a stop in said groove positioned to engage said projection and limit said rotation of said mount about said hub to less than one complete annular rotation of said mount about said hub.

12. The needle assembly of claim 1 wherein elongate needle comprises a sharp distal end and a sharp proximal end, with said needle disposed in said opening in said needle hub so that said sharp distal end projects distally and said sharp proximal end projects proximally from said hub, and wherein said means for releasably attaching said needle hub to the fluid handling device includes male threads on said exterior surface of said hub.

13. The assembly of claim 1 wherein said mount further includes a pusher opposite said hinge means, said pusher extending distally from said mount and disposed to engage a proximal portion of said shield, said pusher being deflectable toward said axis when said latch means is in said unlatched position so that an operator may use said pusher to urge said shield from said closed position to said open position.

14. The assembly of claim 13 wherein said pusher further includes at least one leg disposed to releasably obstruct movement of said tab when said shield is in said latched position thereby substantially preventing inadvertent movement of said latch between said latched position and said unlatched position.

15. The assembly of claim 14 wherein said leg is disposed to releasably obstruct movement of said tab by said pusher having a recess therein to accept said at least pan of said tab when said shield is in said latched position, said tab being placed in and removed from said recess by deflecting said pusher away from said axis.

16. A shielded needle assembly comprising:

an elongate needle having a proximal end, a distal end and a passageway therethrough defining an axis;

a needle hub having a proximal end, a distal end and an outside surface, said needle hub having an axial opening therethrough to receive and hold said needle with said distal end of said needle projecting distally axially therefrom, said proximal end of said needle hub further including means for releasably mounting said needle hub on a fluid handling device;

an elongate shield having a proximal end, a distal end, a sidewall having an elongate opening from said distal end to said proximal end, wherein at least a section of said shield is substantially cylindrical with an exterior surface having an outwardly extending circumferential shoulder, said shoulder being located and sized so that when said latch means is disposed on said shield, said shield being operable between an open position, wherein said needle is exposed for use by passage through said elongate opening, a closed position, wherein said shield substantially obstructs access to said needle, and a latched position, wherein said shield is closed, said elongate opening is substantially obstructed and said shield is substantially prevented from inadvertent movement to said open position;

latch means including a visual indication of said elongate opening being substantially obstructed, said latch means comprising an elongate hollow cylinder with an outwardly extending tab and an inside surface, said cylinder having a open proximal end, a open distal end and a sidewall with an elongate slot from said proximal end to said distal end, therethrough, said hollow cylinder further including a circumferential groove in said inside surface, said hollow cylinder being disposed coaxially about said cylindrical section of said shield so that said shoulder engages said circumferential groove thereby retaining said latch means on said shield and allowing a annular rotation of said latch means with respect said cylindrical section; and hinge means including a mount for retaining said shield onto said needle hub, said mount having an axial passage therethrough sized and shaped to receive at least a portion of said needle hub, said shield movable between said open position and said closed position over said needle by an off-axis pivotal movement about said hinge means, and said shield being latched and unlatched in said closed position by a rotational movement of said latch means with respect to said shield, and wherein said at least a portion of said cylindrical section of said shield has a contrasting color to a color of said latch means so that when said shield is latched with said elongate opening being substantially obstructed, said contrasting color is visible through said elongate slot in said latch means thereby providing said visual indication that said shield is substantially prevented from inadvertent off-axis pivotal movement to expose said needle.

17. The assembly of claim 16 wherein said mount further includes a pusher opposite said hinge means, said pusher extending distally from said mount and disposed to engage a proximal portion of said shield, said pusher being deflectable toward said axis when said latch means is in said unlatched position so that an operator may use said pusher to urge said shield from said closed position to said open position, said pusher further includes at least one leg disposed to releasably obstruct movement of said tab by said pusher having a recess therein to accept said at least part of said tab when said shield is in said latched position, said tab being placed in and removed from said recess in said pusher by deflecting said pusher away from said axis when said shield is in said latched position thereby substantially preventing inadvertent movement of said latch between said latched position and said unlatched position.

18. The shielded needle assembly of claim 16 wherein said means for retaining said mount to said needle hub comprises an annular groove on an inside surface of said axial opening in said mount and said needle hub further comprises an external projection on said portion of said needle hub disposed and sized to engage said groove when said portion of said needle hub is positioned in said opening, said engagement of said projection and said groove retaining said mount on said hub and allowing annular rotation of said mount about said hub; and wherein said groove includes a stop positioned to engage said projection to limit said annular rotation of said mount about said hub to less than about one rotation, thereby facilitating a threading and an unthreading of said hub for mounting and dismounting of said assembly to fluid handling devices.

* * * * *